United States Patent
Bernotas et al.

(10) Patent No.: US 7,259,165 B2
(45) Date of Patent: Aug. 21, 2007

(54) HETEROCYCLYL-3-SULFONYLAZAINDOLE OR-AZAINDAZOLE DERIVATIVES AS 5-HYDROXYTRYPTAMINE-6 LIGANDS

(75) Inventors: Ronald Charles Bernotas, Royersford, PA (US); Yinfa Yan, Bedminster, NJ (US)

(73) Assignee: Wyeth, Madison, NJ (US)

( * ) Notice: Subject to any disclaimer, the term of this patent is extended or adjusted under 35 U.S.C. 154(b) by 545 days.

(21) Appl. No.: 10/778,441

(22) Filed: Feb. 13, 2004

(65) Prior Publication Data

US 2004/0167030 A1 Aug. 26, 2004

Related U.S. Application Data

(60) Provisional application No. 60/447,515, filed on Feb. 14, 2003.

(51) Int. Cl.
*A61K 31/497* (2006.01)
*C07D 487/02* (2006.01)
*C07D 401/04* (2006.01)

(52) U.S. Cl. .................. 514/253.04; 544/262; 544/362

(58) Field of Classification Search ........... 514/253.04; 544/262, 362
See application file for complete search history.

(56) References Cited

U.S. PATENT DOCUMENTS 7,057,039 B2* 6/2006 Bernotas et al. ............ 544/125
2002/0165251 A1 11/2002 Caldirola et al.
2003/0073700 A1 4/2003 Beard et al.
2004/0023970 A1* 2/2004 Bernotas et al. ............ 514/248
2005/0085481 A1* 4/2005 Bernotas et al. ............ 514/248
2006/0142330 A1* 6/2006 Bernotas et al. ............ 514/303

OTHER PUBLICATIONS

Wojciechowski, et al., Synthesis, 1986, vol. 8, pp. 651-653.*

* cited by examiner

*Primary Examiner*—Kamal A. Saeed
*Assistant Examiner*—Nyeemah Grazier
(74) *Attorney, Agent, or Firm*—Barbara L. Lences

(57) ABSTRACT

The present invention provides a compound of formula I and the use thereof for the treatment of a central nervous system disorder related to or affected by the 5-HT6 receptor.

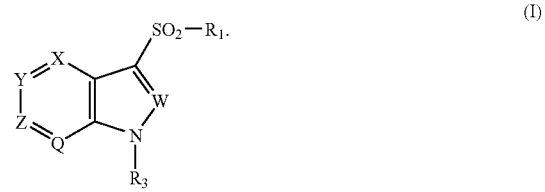

12 Claims, No Drawings

HETEROCYCLYL-3-SULFONYLAZAINDOLE OR-AZAINDAZOLE DERIVATIVES AS 5-HYDROXYTRYPTAMINE-6 LIGANDS

BACKGROUND OF THE INVENTION

This application claims priority from provisional application No. 60/447515 filed on Feb. 14, 2003, the entire disclosure of which is hereby incorporated by reference.

Serotonin (5-Hydroxytryptamine)(5-HT) receptors play a critical role in many physiological and behavioral functions in humans and animals. These functions are mediated through various 5-HT receptors distributed throughout the body. There are now approximately fifteen different human 5-HT receptor subtypes that have been cloned, many with well-defined roles in humans. One of the most recently identified 5-HT receptor subtypes is the 5-HT6 receptor, first cloned from rat tissue in 1993 (Monsma, F. J.; Shen, Y.; Ward, R. P.; Hamblin, M. W. *Molecular Pharmacology* 1993, 43, 320-327) and subsequently from human tissue (Kohen, R.; Metcalf, M. A.; Khan, N.; Druck, T.; Huebner, K.; Sibley, D. R. *Journal of Neurochemistry* 1996, 66, 47-56). The receptor is a G-protein coupled receptor (GPCR) positively coupled to adenylate cyclase (Ruat, M.; Traiffort, E.; Arrang, J-M.; Tardivel-Lacombe, L.; Diaz, L.; Leurs, R.; Schwartz, J-C. *Biochemical Biophysical Research Communications* 1993, 193, 268-276). The receptor is found almost exclusively in the central nervous system (CNS) areas both in rat and in human. In situ hybridization studies of the 5-HT6 receptor in rat brain using mRNA indicate principal localization in the areas of 5-HT projection including striatum, nucleus accumbens, olfactory tubercle, and hippocampal formation (Ward, R. P.; Hamblin, M. W.; Lachowicz, J. E.; Hoffman, B. J.; Sibley, D. R.; Dorsa, D. M. *Neuroscience* 1995, 64,1105-1111).

There are many potential therapeutic uses for 5-HT6 ligands in humans based on direct effects and on indications from available scientific studies. These studies include the localization of the receptor, the affinity of ligands with known in vivo activity, and various animal studies conducted so far.

One potential therapeutic use of modulators of 5-HT6 receptor function is in the enhancement of cognition and memory in human diseases such as Alzheimer's. The high levels of receptor found in important structures in the forebrain, including the caudate/putamen, hippocampus, nucleus accumbens, and cortex suggest a role for the receptor in memory and cognition since these areas are known to play a vital role in memory (Gerard, C.; Martres, M.-P.; Lefevre, K.; Miquel, M. C.; Verge, D.; Lanfumey, R.; Doucet, E.; Hamon, M.; El Mestikawy, S. *Brain Research*, 1997, 746, 207-219). The ability of known 5-HT6 receptor ligands to enhance cholinergic transmission also supported the potential cognition use (Bentley, J. C.; Boursson, A.; Boess, F. G.; Kone, F. C.; Marsden, C. A.; Petit, N.; Sleight, A. J. *British Journal of Pharmacology*, 1999, 126(7), 1537-1542). Studies have found that a known 5-HT6 selective antagonist significantly increased glutamate and aspartate levels in the frontal cortex without elevating levels of noradrenaline, dopamine, or 5-HT. This selective elevation of neurochemicals known to be involved in memory and cognition strongly suggests a role for 5-HT6 ligands in cognition (Dawson, L. A.; Nguyen, H. Q.; Li, P. *British Journal of Pharmacology*, 2000, 130(1), 23-26). Animal studies of memory and learning with a known selective 5-HT6 antagonist found some positive effects (Rogers, D. C.; Hatcher, P. D.; Hagan, J. J. *Society of Neuroscience,* *Abstracts* 2000, 26, 680). Further support for the role of a selective 5-HT6 ligand in cognition can be found in Woolley, M. L.; Marsden, C. A.; Sleight, A. J.; and Fone, K. C. F., *Psychopharmacology*, 2003, 170(4), 358-367.

A related potential therapeutic use for 5-HT6 ligands is the treatment of attention deficit disorders (ADD, also known as Attention Deficit Hyperactivity Disorder or ADHD) in both children and adults. Because 5-HT6 antagonists appear to enhance the activity of the nigrostriatal dopamine pathway and because ADHD has been linked to abnormalities in the caudate (Ernst, M; Zametkin, A. J.; Matochik, J. H.; Jons, P. A.; Cohen, R. M. *Journal of Neuroscience* 1998, 18(15), 5901-5907), 5-HT6 antagonists may attenuate attention deficit disorders.

Early studies examining the affinity of various CNS ligands with known therapeutic utility or a strong structural resemblance to known drugs suggests a role for 5-HT6 ligands in the treatment of schizophrenia and depression. For example, clozapine (an effective clinical antipsychotic) has high affinity for the 5-HT6 receptor subtype. Also, several clinical antidepressants have high affinity for the receptor as well and act as antagonists at this site (Branchek, T. A.; Blackburn, T. P. *Annual Reviews in Pharmacology and Toxicology* 2000, 40, 319-334).

Further, recent in vivo studies in rats indicate 5-HT6 modulators may be useful in the treatment of movement disorders including epilepsy (Stean, T.; Routledge, C.; Upton, N. *British Journal of Pharmacology* 1999, 127 Proc. Supplement 131P and Routledge, C.; Bromidge, S. M.; Moss, S. F.; Price, G. W.; Hirst, W.; Newman, H.; Riley, G.; Gager, T.; Stean, T.; Upton, N.; Clarke, S. E.; Brown, A. M. *British Journal of Pharmacology* 2000, 130(7), 1606-1612).

Taken together, the above studies strongly suggest that compounds which are 5-HT6 receptor modulators, i.e. ligands, may be useful for therapeutic indications including: the treatment of diseases associated with a deficit in memory, cognition, and learning such as Alzheimer's and attention deficit disorder; the treatment of personality disorders such as schizophrenia; the treatment of behavioral disorders, e.g., anxiety, depression and obsessive compulsive disorders; the treatment of motion or motor disorders such as Parkinson's disease and epilepsy; the treatment of diseases associated with neurodegeneration such as stroke and head trauma; or withdrawal from drug addiction including addiction to nicotine, alcohol, and other substances of abuse.

Therefore, it is an object of this invention to provide compounds which are useful as therapeutic agents in the treatment of a variety of central nervous system disorders related to or affected by the 5-HT6 receptor.

It is another object of this invention to provide therapeutic methods and pharmaceutical compositions useful for the treatment of central nervous system disorders related to or affected by the 5-HT6 receptor.

It is a feature of this invention that the compounds provided may also be used to further study and elucidate the 5-HT6 receptor.

These and other objects and features of the invention will become more apparent by the detailed description set forth hereinbelow.

SUMMARY OF THE INVENTION

The present invention provides a heterocyclyl-3-sulfonylazaindole or -azaindazole compound of formula I

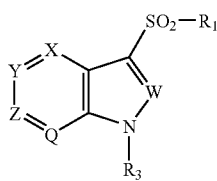

(I)

wherein
- W is N or $CR_2$;
- X is N or $CR_4$;
- Y is N or $CR_5$;
- Z is N or $CR_6$;
- Q is N or $CR_7$ with the proviso that at least one and not more than two of X, Y, Z and Q must be N;
- $R_1$ is an optionally substituted $C_1$-$C_6$alkyl, $C_3$-$C_7$cycloalkyl, aryl, or heteroaryl group or an optionally substituted 8- to 13-membered bicyclic or tricyclic ring system having a N atom at the bridgehead and optionally containing 1, 2 or 3 additional heteroatoms selected from N, O or S;
- $R_2$ is H, halogen, or a $C_1$-$C_6$alkyl, $C_1$-$C_6$alkoxy, $C_3$-$C_7$cycloalkyl, aryl or heteroaryl group each optionally substituted;
- $R_3$ is H or a $C_1$-$C_6$alkyl, $C_3$-$C_7$cycloalkyl, aryl or heteroaryl group each optionally substituted;
- $R_4$, $R_5$, $R_6$ and $R_7$ are each independently H, halogen, CN, $COR_8$, $OCO_2R_9$, $CO_2R_{10}$, $CONR_{11}R_{12}$, $SO_nR_{13}$, $NR_{14}R_{15}$, $OR_{16}$ or a $C_1$-$C_6$alkyl, $C_3$-$C_7$cycloalkyl, aryl or heteroaryl group each optionally substituted or a group M having the structure

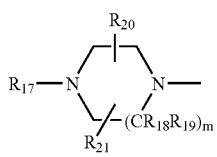

with the proviso that at least one of $R_4$, $R_5$, $R_6$ or $R_7$ must be a group M and with the further proviso that when W is $CR_2$ and X or Z is N, then $R_7$ must be other than a group M;
- $R_8$, $R_9$, $R_{10}$ and $R_{13}$ are each independently H or a $C_1$-$C_6$alkyl, $C_2$-$C_6$alkenyl, $C_2$-$C_6$alkynyl, $C_3$-$C_6$cycloalkyl, cycloheteroalkyl, aryl or heteroaryl group each optionally substituted;
- $R_{11}$, $R_{12}$, $R_{14}$ and $R_{15}$ are each independently H or an optionally substituted $C_1$-$C_4$alkyl group or $R_{11}$ and $R_{12}$ or $R_{14}$ and $R_{15}$ may be taken together with the atom to which they are attached to form a 5- to 7-membered ring optionally containing another heteroatom selected from O, $NR_{22}$ or $SO_n$;
- $R_{16}$ is H or a $C_1$-$C_6$alkyl, $C_2$-$C_6$alkenyl, $C_2$-$C_6$alkynyl, $C_3$-$C_7$cycloalkyl, cycloheteroalkyl, aryl or heteroaryl group each optionally substituted;
- n is 0 or an integer of 1 or 2;
- $R_{17}$ is H or a $C_1$-$C_6$alkyl or $C_3$-$C_7$cycloalkyl group each optionally substituted;
- $R_{18}$, $R_{19}$, $R_{20}$, $R_{21}$ and $R_{23}$ are each independently H or a $C_1$-$C_6$alkyl or $C_3$-$C_7$cycloalkyl group each optionally substituted;
- m is 1 or 2; and
- $R_{22}$ is H or a $C_1$-$C_6$alkyl, $C_2$-$C_6$alkenyl, $C_2$-$C_6$alkynyl, $C_3$-$C_7$cycloalkyl, cycloheteroalkyl, aryl or heteroaryl group each optionally substituted; or the stereoisomers thereof or the pharmaceutically acceptable salts thereof.

The present invention also provides methods and compositions useful for the therapeutic treatment of a central nervous system disorder related to or affected by the 5-HT6 receptor.

DETAILED DESCRIPTION OF THE INVENTION

The 5-hydroxytryptamine-6 (5-HT6) receptor is one of the most recent receptors to be identified by molecular cloning. Its ability to bind a wide range of therapeutic compounds used in psychiatry, coupled with its intriguing distribution in the brain has stimulated significant interest in new compounds which are capable of interacting with or affecting said receptor. Significant efforts are being made to understand the possible role of the 5-HT6 receptor in psychiatry, cognitive dysfunction, motor function and control, memory, mood and the like. To that end, compounds which demonstrate a binding affinity for the 5-HT6 receptor are earnestly sought both as an aid in the study of the 5-HT6 receptor and as potential therapeutic agents in the treatment of central nervous system disorders, for example see C. Reavill and D. C. Rogers, Current Opinion in Investigational Drugs, 2001, 2(1):104-109, Pharma Press Ltd.

Surprisingly, it has now been found that heterocyclyl-3-sulfonylazaindole and -azaindazole derivatives of formula I demonstrate 5-HT6 affinity. Advantageously, said azaindole and azaindazole derivatives may be used as effective therapeutic agents for the treatment of central nervous system (CNS) disorders associated with or affected by the 5-HT6 receptor. Accordingly, the present invention provides 1-heterocyclyl-3-sulfonylazaindole and -azaindazole derivatives of formula I

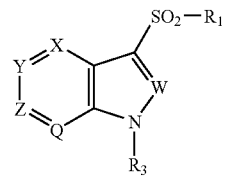

(I)

wherein
- W is N or $CR_2$;
- X is N or $CR_4$;
- Y is N or $CR_5$;
- Z is N or $CR_6$;
- Q is N or $CR_7$ with the proviso that at least one and not more than two of X, Y, Z and Q must be N;
- $R_1$ is an optionally substituted $C_1$-$C_6$alkyl, $C_3$-$C_7$cycloalkyl, aryl, or heteroaryl group or an optionally substituted 8- to 13-membered bicyclic or tricyclic ring system having a N atom at the bridgehead and optionally containing 1, 2 or 3 additional heteroatoms selected from N, O or S;
- $R_2$ is H, halogen, or a $C_1$-$C_6$alkyl, $C_1$-$C_6$alkoxy, $C_3$-$C_7$cycloalkyl, aryl or heteroaryl group each optionally substituted;

$R_3$ is H or a $C_1$-$C_6$alkyl, $C_3$-$C_7$cycloalkyl, aryl, or heteroaryl group each optionally substituted;

$R_4$, $R_5$, $R_6$ and $R_7$ are each independently H, halogen, CN, $COR_8$, $OCO_2R_9$, $CO_2R_{10}$, $CONR_{11}R_{12}$, $SO_nR_{13}$, $NR_{14}R_{15}$, $OR_{16}$ or a $C_1$-$C_6$alkyl, $C_3$-$C_7$cycloalkyl, aryl or heteroaryl group each optionally substituted or a group M having the structure

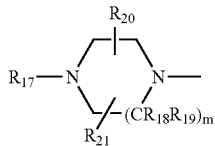

with the proviso that at least one of $R_4$, $R_5$, $R_6$ or $R_7$ must be a group M and with the further proviso that when W is $CR_2$ and X or Z is N, then $R_7$ must be other than a group M;

$R_8$, $R_9$, $R_{10}$ and $R_{13}$ are each independently H or a $C_1$-$C_6$alkyl, $C_2$-$C_6$alkenyl, $C_2$-$C_6$alkynyl, $C_3$-$C_6$cycloalkyl, cycloheteroalkyl, aryl or heteroaryl group each optionally substituted;

$R_{11}$, $R_{12}$, $R_{14}$ and $R_{15}$ are each independently H or an optionally substituted $C_1$-$C_4$alkyl group or $R_{11}$, and $R_{12}$ or $R_{14}$ and $R_{15}$ may be taken together with the atom to which they are attached to form a 5- to 7-membered ring optionally containing another heteroatom selected from O, $NR_{22}$ or $SO_n$;

$R_{16}$ is H or a $C_1$-$C_6$alkyl, $C_2$-$C_6$alkenyl, $C_2$-$C_6$alkynyl, $C_3$-$C_7$cycloalkyl, cycloheteroalkyl, aryl or heteroaryl group each optionally substituted;

n is 0 or an integer of 1 or 2;

$R_{17}$ is H or a $C_1$-$C_6$alkyl or $C_3$-$C_7$cycloalkyl group each optionally substituted;

$R_{18}$, $R_{19}$, $R_{20}$, $R_{21}$ and $R_{23}$ are each independently H or a $C_1$-$C_6$alkyl or $C_3$-$C_7$cycloalkyl group each optionally substituted;

m is 1 or 2; and $R_{22}$ is H or a $C_1$-$C6$alkyl, $C_2$-$C_6$alkenyl, $C_2$-$C_6$alkynyl, $C_3$-$C_7$cycloalkyl, cycloheteroalkyl, aryl or heteroaryl group each optionally substituted; or the stereoisomers thereof or the pharmaceutically acceptable salts thereof.

As used in the specification and claims, the term halogen designates F, Cl, Br or I and the term cycloheteroalkyl designates a five- to seven-membered cycloalkyl ring system containing 1 or 2 heteroatoms, which may be the same or different, selected from N, O or S and optionally containing one double bond. Exemplary of the cycloheteroalkyl ring systems included in the term as designated herein are the following rings wherein X is NR, O or S; and R is H or an optional substituent as described hereinbelow:

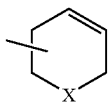 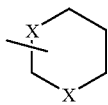 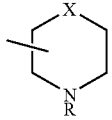

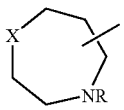

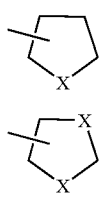 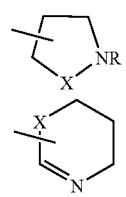 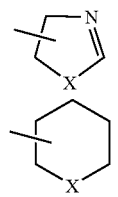

-continued

Similarly, as used in the specification and claims, the term heteroaryl designates a five- to ten-membered aromatic ring system containing 1, 2 or 3 heteroatoms, which may be the same or different, selected from N, O or S. Such heteroaryl ring systems include pyrrolyl, azolyl, oxazolyl, thiazolyl, imidazolyl, furyl, thienyl, quinolinyl, isoquinolinyl, indolyl, benzothienyl, benzofuranyl, benzisoxazolyl or the like. The term aryl designates a carbocyclic aromatic ring system such as phenyl, naphthyl, anthracenyl or the like. The term haloalkyl as used herein designates a $C_nH_{2n+1}$ group having from one to 2n+1 halogen atoms which may be the same or different and the term haloalkoxy as used herein designates an $OC_nH_{2n+1}$ group having from one to 2n+1 halogen atoms which may be the same or different.

Exemplary of the 8- to 13-membered bicyclic or tricyclic ring systems having a N atom at the bridgehead and optionally containing 1, 2 or 3 additional heteroatoms selected from N, O or S included in the term as designated herein are the following ring systems wherein $W_2$ is NR, O or S; and R is H or an optional substituent as described hereinbelow:

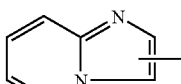 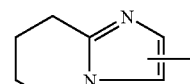
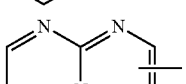 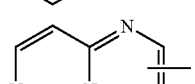
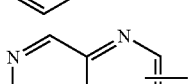 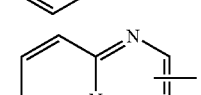
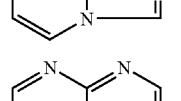 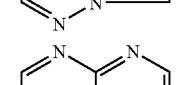
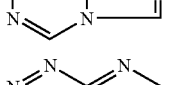 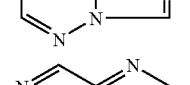
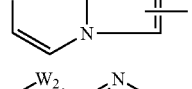 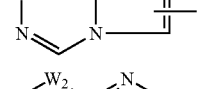
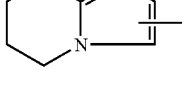 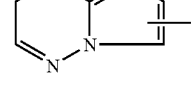
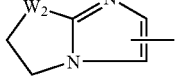 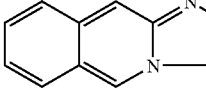

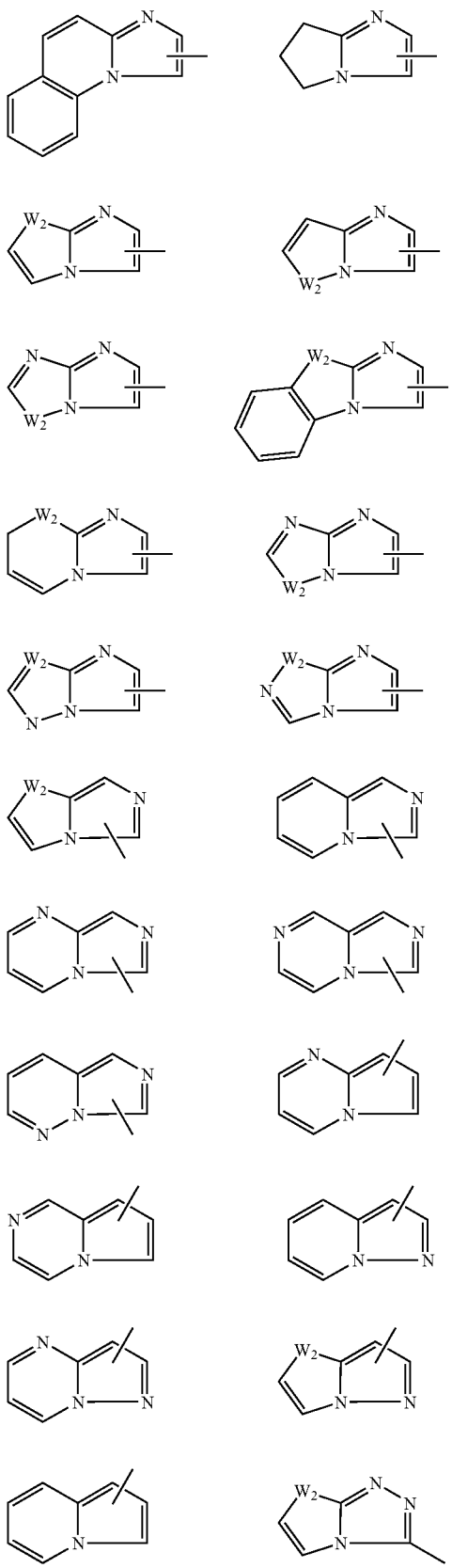

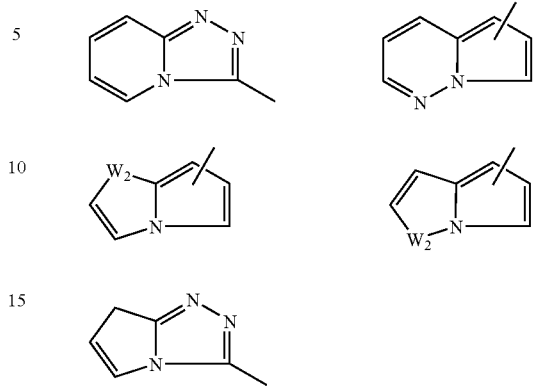

In the specification and claims, when the terms $C_1$-$C_6$alkyl, $C_2$-$C_6$alkenyl, $C_2$-$C_6$alkynyl, $C_3$-$C_7$cycloalkyl, cycloheteroalkyl, aryl or heteroaryl as designated as being optionally substituted, the substituent groups which are optionally present may be one or more of those customarily employed in the development of pharmaceutical compounds or the modification of such compounds to influence their structure/activity, persistence, absorption, stability or other beneficial property. Specific examples of such substituents include halogen atoms, nitro, cyano, thiocyanato, cyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsuphinyl, alkylsulphonyl, carbamoyl, alkylamido, phenyl, phenoxy, benzyl, benzyloxy, heterocyclyl or cycloalkyl groups, preferably halogen atoms or lower alkyl or lower alkoxy groups. Typically, 0-3 substituents may be present. When any of the foregoing substituents represents or contains an alkyl substituent group, this may be linear or branched and may contain up to 12, preferably up to 6, more preferably up to 4 carbon atoms.

Pharmaceutically acceptable salts may be any acid addition salt formed by a compound of formula I and a pharmaceutically acceptable acid such as phosphoric, sulfuric, hydrochloric, hydrobromic, citric, maleic, malonic, mandelic, succinic, fumaric, acetic, lactic, nitric, sulfonic, p-toluene sulfonic, methane sulfonic acid or the like.

Compounds of the invention include esters, carbamates or other conventional prodrug forms, which in general, are functional derivatives of the compounds of the invention and which are readily converted to the inventive active moiety in vivo. Correspondingly, the method of the invention embraces the treatment of the various conditions described hereinabove with a compound of formula I or with a compound which is not specifically disclosed but which, upon administration, converts to a compound of formula I in vivo. Also included are metabolites of the compounds of the present invention defined as active species produced upon introduction of these compounds into a biological system.

Compounds of the invention may exist as one or more stereoisomers. The various stereoisomers include enantiomers, diastereomers, atropisomers and geometric isomers. One skilled in the art will appreciate that one stereoisomer may be more active or may exhibit beneficial effects when enriched relative to the other stereoisomer(s) or when separated from the other stereoisomer(s). Additionally, the skilled artisan knows how to separate, enrich or selectively prepare said stereoisomers. Accordingly, the present invention comprises compounds of Formula I, the stereoisomers thereof and the pharmaceutically acceptable salts thereof. The compounds of the invention may be present as a mixture of stereoisomers, individual stereoisomers, or as an optically active or enantiomerically pure form.

Preferred compounds of the invention are those compounds of formula I wherein m is 1. Also preferred are those compounds of formula I wherein Y is $CR_5$ and $R_5$ is a group M. Another group of preferred compounds of formula I are those compounds wherein W is N; Q is $CR_7$ and $R_7$ is a group M.

More preferred compounds of the invention are those formula I compounds wherein m is 1; Y is $CR_5$ and $R_5$ is a group M. Another group of more preferred compounds are those formula I compounds wherein W is N; m is 1; Q is $CR_7$ and $R_7$ is a group M. Further more preferred formula I compounds are those compounds wherein m is 1; $R_5$ is a group M and $R_1$ is an optionally substituted phenyl, naphthyl or heteroaryl group.

Examples of preferred compounds of formula I include:
5-(4-benzylpiperazin-1-yl)-3-(phenylsulfonyl)-1H-pyrrolo[2,3-b]pyridine;
5-(4-methylpiperazin-1-yl)-3-(phenylsulfonyl)-1H-pyrrolo[2,3-c]pyridine;
3-(phenylsulfonyl)-5-(4-propylpiperazin-1-yl)-1H-pyrrolo[2,3-b]pyridine;
3-(phenylsulfonyl)-5-piperazin-1-yl-1H-pyrrolo[2,3-b]pyridine;
3[-(3-cyanophenyl)sulfonyl]-5-piperazin-1-yl-1H-pyrrolo[2,3-b]pyridine;
5-(4-benzylpiperazin-1-yl)-3-[(1-naphthyl)sulfonyl]-1H-pyrrolo[3,2-c]pyridine;
5-(4-methylpiperazin-1-yl)-3-[(2-naphthyl)sulfonyl]-1H-pyrrolo[3,2-b]pyridine;
3-[(2-chloro-4-fluorophenyl)sulfonyl]-5-(4-propylpiperazin-1-yl)-1H-pyrrolo[2,3-b]pyridine;
1-methyl-3-(phenylsulfonyl)-5-piperazin-1-yl-1H-pyrrolo[3,2-b]pyridine;
1-phenyl-3-(phenylsulfonyl)-5-piperazin-1-yl-1H-pyrrolo[2,3-c]pyridine;
5-(4-benzylpiperazin-1-yl)-3-[(3-fluorophenyl)sulfonyl]-1H-pyrrolo[3,2-c]pyridine;
3-[(4-fluorophenyl)sulfonyl]-5-(4-methylpiperazin-1-yl)-1H-pyrrolo[3,2-b]pyridine;
3-[(2-chlorophenyl)sulfonyl]-5-(4-propylpiperazin-1-yl)-1H-pyrrolo[2,3-b]pyridine;
3-[(4-aminophenyl)sulfonyl]-5-piperazin-1-yl-1H-pyrrolo[2,3-b]pyridine;
2-methyl-3-(phenylsulfonyl)-5-piperazin-1-yl-1H-pyrrolo[2,3-b]pyridine;
4-chloro-3-(phenylsulfonyl)-5-piperazin-1-yl-1H-pyrrolo[2,3-b]pyridine;
7-fluoro-3-(phenylsulfonyl)-5-piperazin-1-yl-1H-pyrrolo[2,3-b]pyridine;
6-fluoro-3-(phenylsulfonyl)-5-piperazin-1-yl-1H-pyrrolo[2,3-c]pyridine;
6-(4-benzylpiperazin-1-yl)-3-(phenylsulfonyl)-1H-pyrrolo[3,2-c]pyridine;
6-(4-methylpiperazin-1-yl)-3-(phenylsulfonyl)-1H-pyrrolo[3,2-b]pyridine;
3-(phenylsulfonyl)-6-(4-propylpiperazin-1-yl)-1H-pyrrolo[2,3-b]pyridine;
3-(phenylsulfonyl)-6-piperazin-1-yl-1H-pyrrolo[2,3-b]pyridine;
4-(4-benzylpiperazin-1-yl)-3-(phenylsulfonyl)-1H-pyrrolo[2,3-b]pyridine;
4-(4-methylpiperazin-1-yl)-3-(phenylsulfonyl)-1H-pyrrolo[2,3-b]pyridine;
3-(phenylsulfonyl)-4-(4-propylpiperazin-1-yl)-1H-pyrrolo[3,2-c]pyridine;
3-(phenylsulfonyl)-4-piperazin-1-yl-1H-pyrrolo[3,2-b]pyridine;
3-(phenylsulfonyl)-7-piperazin-1-yl-1H-pyrazolo[4,3-b]pyridine;
3-[(1-naphthyl)sulfonyl]-5-piperazin-1-yl-1H-pyrazolo[4,3-b]pyridine;
3-(phenylsulfonyl)-5-piperazin-1-yl-1H-pyrazolo[4,3-b]pyridine;
3-[(3-fluorophenyl)sulfonyl]-5-piperazin-1-yl-1H-pyrazolo[4,3-b]pyridine;
3-[(3-fluorophenyl)sulfonyl]-7-piperazin-1-yl-1H-pyrazolo[4,3-b]pyridine;
3-(phenylsulfonyl)-7-piperazin-1-yl-1H-pyrazolo[3,4-c]pyridine;
3-[(1-naphthyl)sulfonyl]-7-piperazin-1-yl-1H-pyrazolo[3,4-c]pyridine;
3-(2-thienylsulfonyl)-7-piperazin-1-yl-1H-pyrazolo[3,4-c]pyridine;
3-[(3-fluorophenyl)sulfonyl]-1-methyl-7-piperazin-1-yl-1H-pyrazolo[3,4-c]pyridine;
3-[(3-fluorophenyl)sulfonyl]-7-piperazin-1-yl-1H-pyrazolo[3,4-c]pyridine;
3-(phenylsulfonyl)-5-piperazin-1-yl-1H-pyrazolo[3,4-c]pyridine;
3-[(1-naphthyl)sulfonyl]-5-piperazin-1-yl-1H-pyrazolo[3,4-c]pyridine;
3-(phenylsulfonyl)-7-piperazin-1-yl-1H-pyrazolo[4,3-c]pyridine;
3-[(1-naphthyl)sulfonyl]-7-piperazin-1-yl-1H-pyrazolo[4,3-c]pyridine;
3-(2-thienylsulfonyl)-7-piperazin-1-yl-1H-pyrazolo[4,3-c]pyridine;
3-[(3-fluorophenyl)sulfonyl]-1-methyl-7-piperazin-1-yl-1H-pyrazolo[4,3-c]pyridine;
3-[(3-fluorophenyl)sulfonyl]-7-piperazin-1-yl-1H-pyrazolo[4,3-c]pyridine;
3-(phenylsulfonyl)-5-piperazin-1-yl-1H-pyrazolo[3,4-b]pyridine;
3-[(1-naphthyl)sulfonyl]-5-piperazin-1-yl-1H-pyrazolo[3,4-b]pyridine;
3-(2-thienylsulfonyl)-5-piperazin-1-yl-1H-pyrazolo[3,4-b]pyridine;
3-[(3-fluorophenyl)sulfonyl]-1-methyl-5-piperazin-1-yl-1H-pyrazolo[3,4-b]pyridine;
3-[(3-fluorophenyl)sulfonyl]-5-piperazin-1-yl-1H-pyrazolo[3,4-b]pyridine;

the stereoisomers thereof; or the pharmaceutically acceptable salts thereof.

Compounds of the invention may be prepared using conventional synthetic methods and, if required, standard separation or isolation techniques. For example, compounds of formula I wherein $R_3$ is H and W is $CR_2$ (Ia) may be prepared by reacting a nitropyridine compound of formula II with reducing agents such as Fe, Zn or Sn in the presence of an acid to give the amine of formula III; reacting said amine with an appropriate orthoester of formula IV to give the formula V compound; and cyclizing the formula V compound in the presence of a base to give the desired azaindole product of formula Ia. Methods known to prepare 3-sulfonylazaindoles are described by Wojciechowski, K. and Makosza, M., Synthesis 1986, 651-653 and by Orlemans, E. O. M.; Schreuder, A. H.; Conti, P. G. M.; Verboom, W.; and Reinhoudt, D. N., Tetrahedron 1987, 43, 3817-3826. In a similar manner, the formula III amine may be reacted with $NaNO_2$ in the presence of an acid to give those compounds of formula I wherein $R_3$ is H and W is N (Ib). The reactions are shown in flow diagram I.

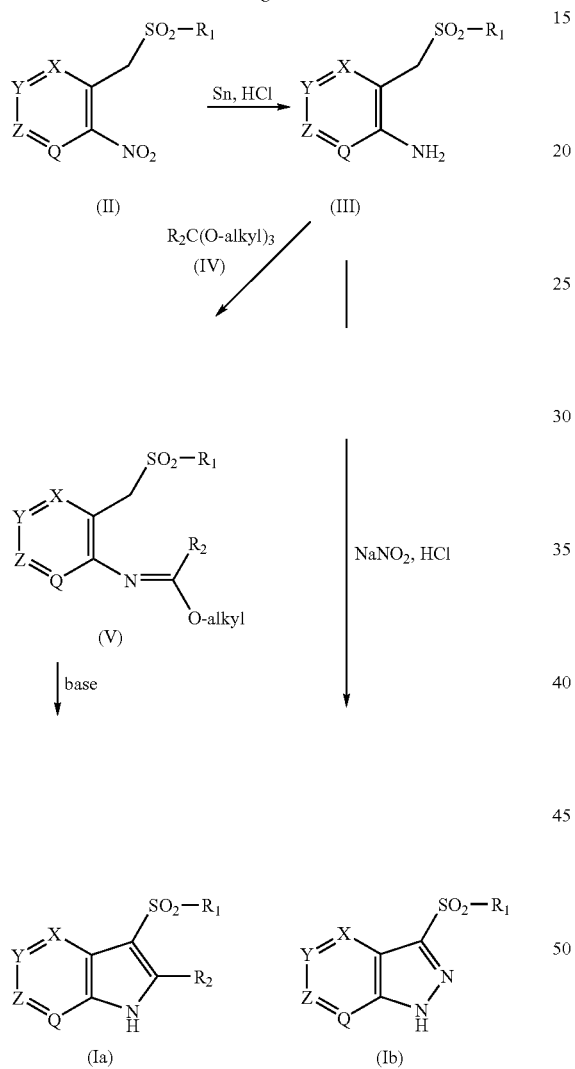

Compounds of formula II wherein Z is N; Y is $CR_5$ and $R_5$ is a group M (IIa) may be prepared by reacting a nitropyridine of formula VI with a diazacyclic compound of formula VII in the presence of a base such as $K_2CO_3$ to give the formula IIa compound. The formula IIa compound may then be reduced and cyclized as described hereinabove in flow diagram I to give compounds of formula I wherein Z is N; Y is $CR_5$; and $R_5$ is a group M (Ic). The reactions are shown in flow diagram II wherein Hal represents chlorine, bromine or fluorine.

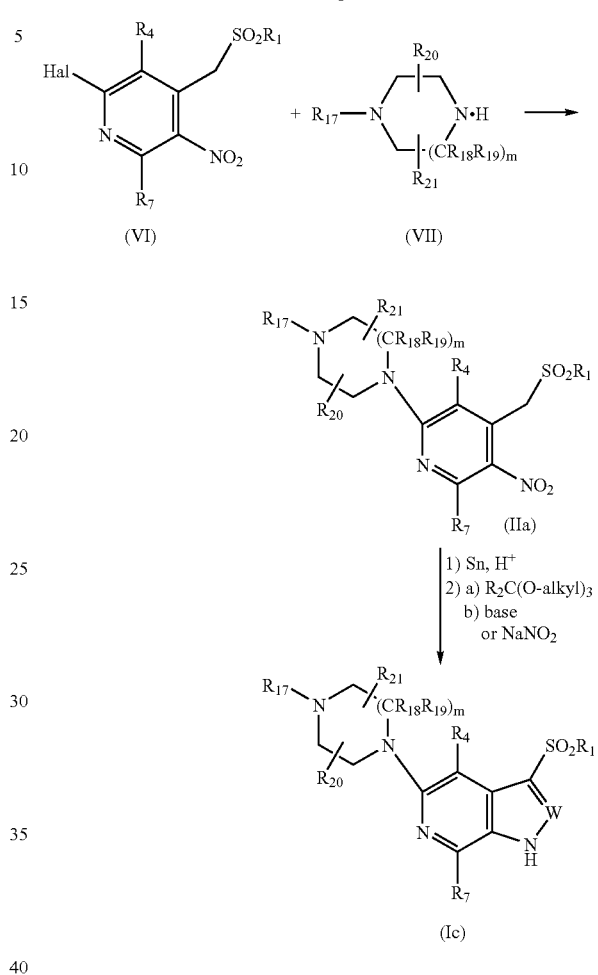

Alternatively, compounds of formula Ic may be prepared directly from an azaindole or azaindazole compound of formula VIII by coupling the formula VIII substrate with a diazacyclic compound of formula VII in the presence of a catalyst, such as a palladium catalyst, to give the protected compound of formula IX and deprotecting the formula IX compound to give the desired compound of formula Ic. The reaction is shown in flow diagram III wherein LG represents a leaving group such as iodine, bromine, chlorine or an activated hydroxyl group, for example a triflate ($CF_3SO_3^-$) and P is a protecting group.

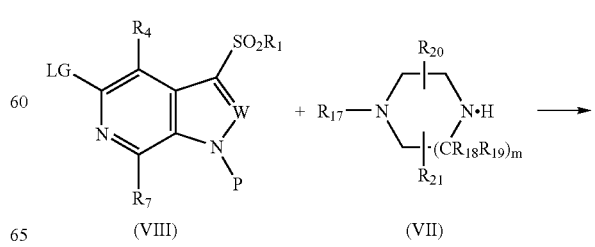

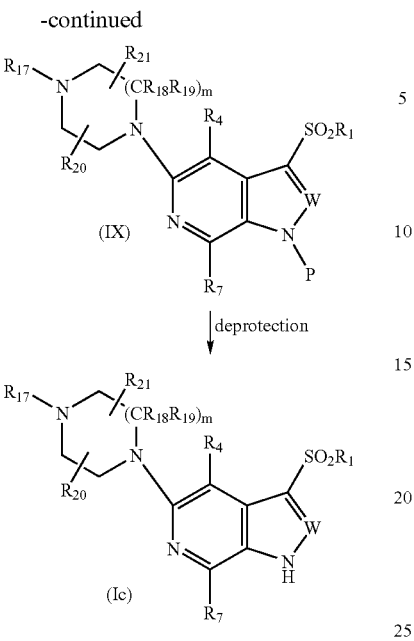

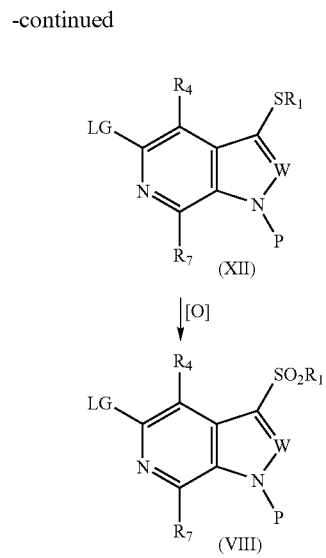

Compounds of formula VIII, or the isosteres or regisomers thereof, may be prepared by conventional methods. For example, a protected azaindole or azaindazole of formula X may be reacted with a methylsulfonyl compound of formula XI to give the 3-thio compound of formula XII; said 3-thio compound may be oxidized using a conventional oxidizing agent such as $H_2O_2$, m-chloroperbenzoic acid or the like to give the corresponding 3-sulfonyl compound of formula VIII. The reaction is shown in flow diagram IV wherein LG and P are as described hereinabove.

Flow Diagram IV

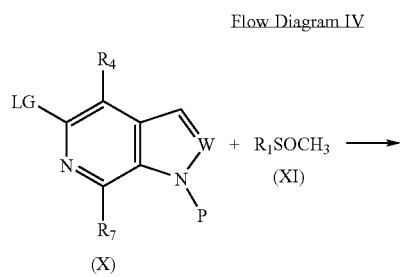

Compounds of formula Ib or Ic wherein $R_3$ is other than H may be prepared using conventional alkylation/deprotection or coupling procedures, such as a Suzuki-type coupling. For example, compounds of formula I wherein Y is N; Z is $CR_6$; $R_6$ is a group M; and $R_3$ is other than H (Id) may be prepared by reacting a protected compound of formula XIII with an alkylating agent of formula XIV in the presence of a base and a solvent optionally in the presence of a phase-transfer agent to give the protected alkylated compound of formula XV and deprotecting said formula XV compound to give the desired compound of formula Id wherein $R_{17}$ is H; optionally this compound may be reacted with an alkylating agent of formula XVI under standard alkylation conditions to give the compound of formula Id wherein $R_{17}$ is other than H. If desired, the sequence may be reversed by deprotecting the formula XIV compound to give the compound of formula I wherein $R_3$ and $R_{17}$ are H (Ie) and alkylating the formula Ie compound with the formula XVI alkylating agent to give the compound of formula Id. The reactions are shown in flow diagram V wherein P is a protecting group and LG' is a leaving group such as Cl, Br, I, OH, tosyl, mesyl or the like.

Flow Diagrams V

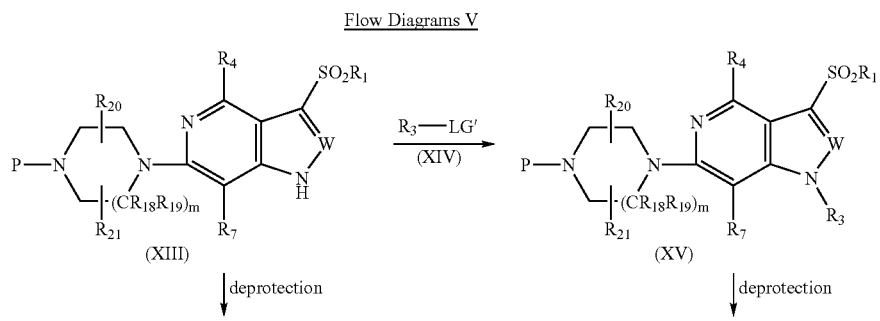

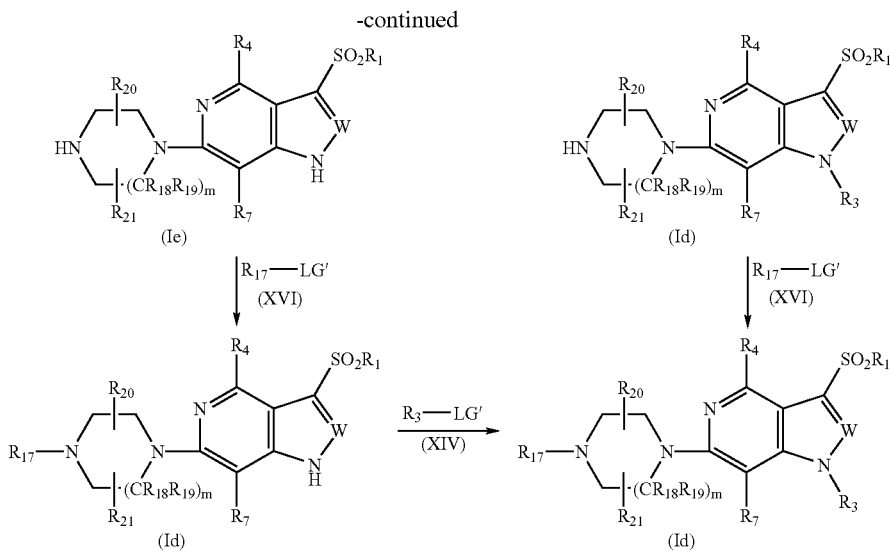

It is understood that the reaction sequences shown in flow diagrams II, III, IV and V are applicable to the corresponding isosteres wherein any one of X, Y, Z or Q may represent N or to the corresponding regio isomers wherein any one of $R_4$, $R_5$, $R_6$ or $R_7$ may represent a group M.

Protecting groups suitable for use in the reactions shown hereinabove include t-butyloxycarbonyl, benzyl, acetyl, benzyloxycarbonyl, or any conventional group known to protect a basic nitrogen in standard synthetic procedures.

Advantageously, the formula I compounds of the invention are useful for the treatment of CNS disorders related to or affected by the 5-HT6 receptor, including motor, mood, personality, behavioral, psychiatric, cognitive, neurodegenerative, or the like disorders, for example Alzheimer's disease, Parkinson's disease, attention deficit disorder, anxiety, epilepsy, depression, obsessive compulsive disorder, sleep disorders, neurodegenerative disorders (such as head trauma or stroke), feeding disorders (such as anorexia or bulimia), schizophrenia, memory loss, disorders associated with withdrawal from drug or nicotine abuse, or the like or certain gastrointestinal disorders such as irritable bowel syndrome. Accordingly, the present invention provides a method for the treatment of a disorder of the central nervous system related to or affected by the 5-HT6 receptor in a patient in need thereof which comprises providing said patient a therapeutically effective amount of a compound of formula I as described hereinabove. The compounds may be provided by oral or parenteral administration or in any common manner known to be an effective administration of a therapeutic agent to a patient in need thereof.

The term "providing" as used herein with respect to providing a compound or substance embraced by the invention, designates either directly administering such a compound or substance, or administering a prodrug, derivative or analog which forms an equivalent amount of the compound or substance within the body.

The therapeutically effective amount provided in the treatment of a specific CNS disorder may vary according to the specific condition(s) being treated, the size, age and response pattern of the patient, the severity of the disorder, the judgment of the attending physician and the like. In general, effective amounts for daily oral administration may be about 0.01 to 1,000 mg/kg, preferably about 0.5 to 500 mg/kg and effective amounts for parenteral administration may be about 0.1 to 100 mg/kg, preferably about 0.5 to 50 mg/kg.

In actual practice, the compounds of the invention are provided by administering the compound or a precursor thereof in a solid or liquid form, either neat or in combination with one or more conventional pharmaceutical carriers or excipients. Accordingly, the present invention provides a pharmaceutical composition which comprises a pharmaceutically acceptable carrier and an effective amount of a compound of formula I as described hereinabove.

Solid carriers suitable for use in the composition of the invention include one or more substances which may also act as flavoring agents, lubricants, solubilizers, suspending agents, fillers, glidants, compression aides, binders, tablet-disintegrating agents or encapsulating materials. In powders, the carrier may be a finely divided solid which is in admixture with a finely divided compound of formula I. In tablets, the formula I compound may be mixed with a carrier having the necessary compression properties in suitable proportions and compacted in the shape and size desired. Said powders and tablets may contain up to 99% by weight of the formula I compound. Solid carriers suitable for use in the composition of the invention include calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Any pharmaceutically acceptable liquid carrier suitable for preparing solutions, suspensions, emulsions, syrups and elixirs may be employed in the composition of the invention. Compounds of formula I may be dissolved or suspended in a pharmaceutically acceptable liquid carrier such as water, an organic solvent, or a pharmaceutically acceptable oil or fat, or a mixture thereof. Said liquid composition may contain other suitable pharmaceutical additives such as solubilizers, emulsifiers, buffers, preservatives, sweeteners, flavoring agents, suspending agents, thickening agents, coloring agents, viscosity regulators, stabilizers, osmo-regulators, or the like. Examples of liquid carriers suitable for oral and parenteral administration include water (particularly containing additives as above, e.g., cellulose derivatives, preferably sodium carboxymethyl cellulose solution), alcohols (including monohydric alcohols and polyhydric alcohols, e.g., glycols) or their derivatives, or oils (e.g., fractionated coconut oil and arachis oil). For parenteral administration the carrier may also be an oily ester such as ethyl oleate or isopropyl myristate.

Compositions of the invention which are sterile solutions or suspensions are suitable for intramuscular, intraperitoneal or subcutaneous injection. Sterile solutions may also be administered intravenously. Inventive compositions suitable for oral administration may be in either liquid or solid composition form.

For a more clear understanding, and in order to illustrate the invention more clearly, specific examples thereof are set forth hereinbelow. The following examples are merely illustrative and are not to be understood as limiting the scope and underlying principles of the invention in any way.

The term NMR designates proton nuclear magnetic resonance. The terms DMF and EtOAc designate dimethyl formamide and ethyl acetate, respectively. The term THF designates tetrahydrofuran. In the structures, the term Ph designates a phenyl group.

EXAMPLE 1

Preparation of 1-Methyl-4-(5-nitropyridin-2-yl)piperazine

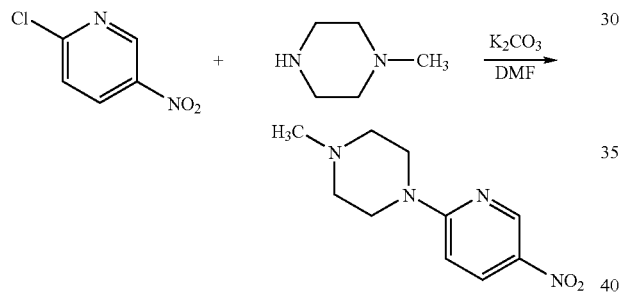

A stirred mixture of 2-chloro-5-nitropyridine (3.16 g, 20.0 mmol), 1-methyl-piperazine (2.00 g, 2.00 mmol) and potassium carbonate (2.76 g, 20.0 mmol) in DMF is heated at 100° C. for 24 h, cooled, poured into water and extracted with CH$_2$Cl$_2$. The combined extracts are dried over MgSO$_4$ and concentrated in vacuo. The resultant residue is purified by flash chromatography (SiO$_2$, 2% ammonia in 10:90 ethanol:ethyl acetate as eluent) affords the title compound as an off-white solid, 4.0 g (90% yield), identified by NMR analysis.

EXAMPLE 2

Preparation of 1-Methyl-4-{5-nitro-6-[(phenylsulfonyl)methyl]pyridin-2-yl}piperazine

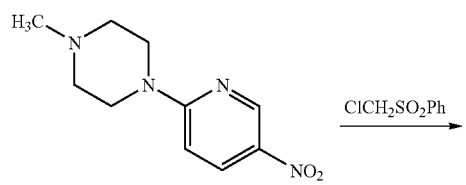

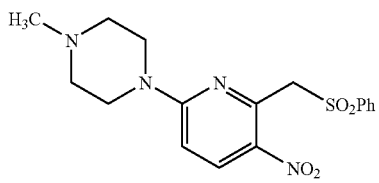

A stirred solution of 1-methyl-4-(5-nitropyridin-2-yl)piperazine (1.10 g, 5.00 mmol) and chloromethylphenylsulfone (0.950 g, 5.00 mmol) in dry THF, under nitrogen, is cooled to −60° C., treated with 1.0 M KO$^t$Bu in THF (10.0 mL, 10.0 mmol), allowed to warm to −10° C. over a 1 h period, quenched with acetic acid, treated sequentially with water and saturated aqueous NaHCO$_3$ and extracted with CH$_2$Cl$_2$. The combined extracts are washed sequentially with water and brine, dried over MgSO$_4$ and concentrated in vacuo. The resultant residue is crystallized from EtOAc to give the title compound as a yellow solid, 1.60 g (85% yield), mp: 170°-172° C., identified by mass spectral and NMR analyses.

EXAMPLE 3

Preparation of 6-(4-Methylpiperazin-1-yl)-2-[(phenylsulfonyl)methyl]pyridin-3-yl-amine

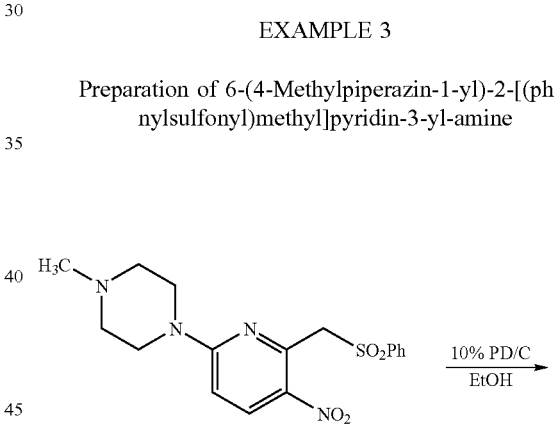

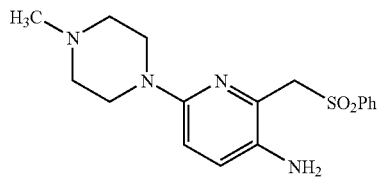

A mixture of 1-methyl-4-{5-nitro-6-[(phenylsulfonyl)methyl]pyridin-2-yl}-piperazine (1.60 g, 4.35 mmol) and 10% Pd/C (200 mg) in a 1:1 mixture of ethanol:THF is hydrogenated at 45 psi for 4 h at ambient temperatures. The catalyst is filtered off and the filtrate is concentrated in vacuo to afford the title compound as a yellow solid, 1.45 g (99% yield), identified by NMR analysis.

EXAMPLE 4

Preparation of 5-(4-methylpiperazin-1-yl)-3-(phenylsulfonyl)-1H-pyrazolo-[4,3-b]pyridine hydrochloride

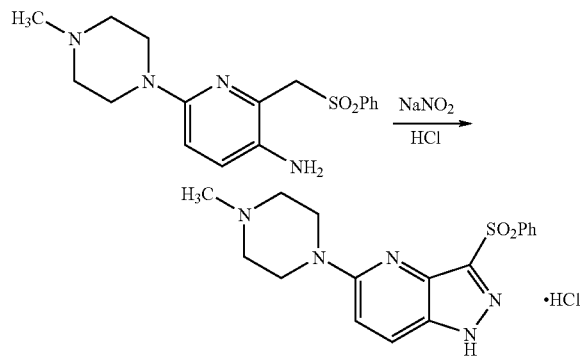

A stirred solution of 2-[(phenylsulfonyl)methyl]-6-(4-methylpiperazin-1-yl)-pyridin-3-ylamine (1.20 g, 3.50 mmol) in 1.0 M aqueous hydrochloric acid (20 mL) is cooled in an ice bath, treated dropwise with NaNO$_2$ (358 mg, 5.2 mmol) in water, stirred for 1 h, treated with aqueous saturated NaHCO$_3$ and filtered. The brown solid filtercake is washed with water, dried in vacuo, triturated with acetone and filtered. The filtercake is washed with ether and air-dried to afford the free amine of the title compound as a tan solid, 0.50 g. This solid is dissolved in a mixture of ethanol and 4.0 M HCl in dioxane and concentrated in vacuo. The resultant residue is triturated with ether to afford the title compound as an off-white solid, mp>250° C., identified by mass spectral and NMR analyses.

EXAMPLE 5

Preparation of 2-Chloro-5-nitro-6-[(phenylsulfonyl)methyl]pyridine (A) and 2-Chloro-5-nitro-4-[(phenylsulfonyl)methyl]pyridine (B)

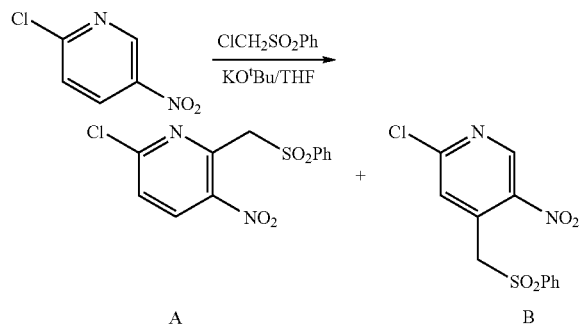

A stirred solution of 2-chloro-5-nitro-pyridine (3.97 g, 25.0 mmol) and chloromethylphenylsulfone (4.76 g, 25.0 mmol) in dry THF at −65° C. under nitrogen is treated with 1.0M KO-t-Bu in THF (55.0 mL, 55.0 mmol), allowed to warm to 0° C. over 1.5 h, treated with glacial acetic acid (5.5 mL), stirred for 0.5 h, treated with saturated aqueous NaHCO$_3$, stirred for 2 h, and extracted with CH$_2$Cl$_2$. The combined extracts are washed with brine, dried over MgSO$_4$ and concentrated in vacuo to afford a brown oil. The oil is chromatographed (silica gel, 50:50 EtOAc:hexanes as eluent) to give a slightly yellow solid identified by NMR as a mixture of the two title regioisomers A and B (5.67 g, 73%). A second chromatography (silica gel, 40:60 EtOAc:hexanes as eluent) provides the title compound A as a white solid, 1.75 g (23% yield), identified by NMR and mass spectral analyses and the title compound B as a white solid, 0.79 g (10% yield), identified by NMR and mass spectral analyses.

EXAMPLE 6

Preparation of 6-(4-Benzylpiperazin-1-yl)-3-nitro-2-[(phenylsulfonyl)methyl]-pyridine

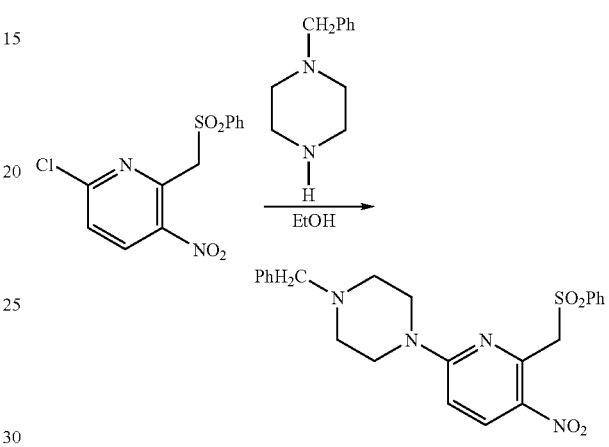

A stirred mixture of 2-chloro-5-nitro-6-[(phenylsulfonyl)methyl]pyridine (1.41 g, 4.50 mmol), 1-benzylpiperazine (0.873 g, 4.95 mmol), and K$_2$CO$_3$ (0.683 g, 4.95 mmol) in ethanol is heated at reflux temperature for 1.5 h, cooled, diluted with water and extracted with CH$_2$Cl$_2$. The extracts are combined, dried over MgSO$_4$ and concentrated in vacuo. The resultant residue is chromatographed (silica gel, EtOAc as eluent) to afford the title compound as an orange-yellow solid, 1.96 g (96% yield), mp 175-176° C., identified by NMR and mass spectral analyses.

EXAMPLE 7

Preparation of 3-Amino-6-(4-benzylpiperazin-1-yl)-2-[(phenylsulfonyl)methyl]-pyridine

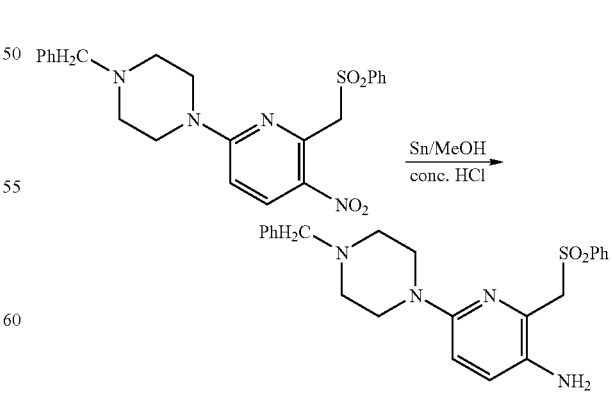

A stirred mixture of 6-(4-benzylpiperazin-1-yl)-3-nitro-2-[(phenylsulfonyl)-methyl]pyridine (1.81 g, 4.00 mmol) and granular tin (2.09 g, 17.6 mmol) in methanol is treated with conc. HCl, heated under nitrogen at 50° C. for 7 h, stirred at ambient temperatures for 16 h, poured into aqueous NaHCO$_3$ and extracted with EtOAc. The combined extracts are dried over MgSO$_4$ and concentrated in vacuo. The resultant residue is chromatographed (silica gel, EtOAc as eluent) to afford the title compound as a yellow solid, 1.47 g (87% yield), mp 175-176° C., identified by NMR and mass spectral analyses.

EXAMPLE 8

Preparation of 5-(4-Benzylpiperazin-1-yl)-3-(phenylsulfonyl)-1H-pyrrolo[3,2-b]pyridine

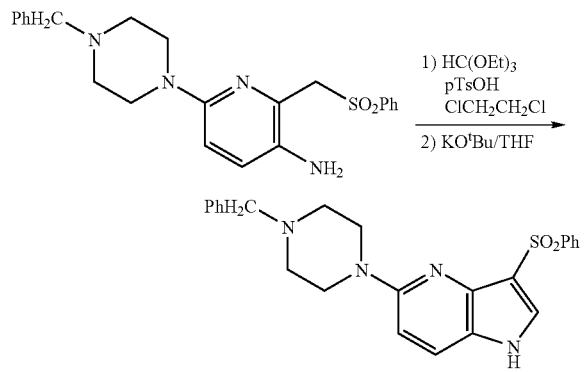

A stirred solution of 3-amino-6-(4-benzylpiperazin-1-yl)-2-[(phenylsulfonyl)-methyl]pyridine (1.41 g, 3.34 mmol), p-toluenesulfonic acid monohydrate (63 mg, 0.33 mmol), triethyl orthoformate (2.78 mL, 16.7 mmol) in 1,2-dichloroethane is heated at reflux temperature under nitrogen for 7.5 h, stirred at room temperature for 16 h and in vacuo to afford an oil residue. The residue is stirred in dry THF, treated with 1.0M KO-t-Bu in THF (4.35 mL, 4.35 mmol) for 2 h, treated sequentially with saturated aqueous NH$_4$Cl, saturated aqueous NaHCO$_3$ and water and extracted with CH$_2$Cl$_2$. The combined extracts are dried over MgSO$_4$ and concentrated in vacuo to give a yellow solid residue. This residue is chromatograped (silica gel, EtOAc as eluent to afford the title compound as a pale yellow solid, 1.18 g (79% yield), mp 238-239° C., identified by NMR and mass spectral analyses.

EXAMPLE 9

Preparation 3-(Phenylsulfonyl)-5-piperazin-1-yl-1H-pyrrolo[3,2-b]pyridine Dihydrochloride

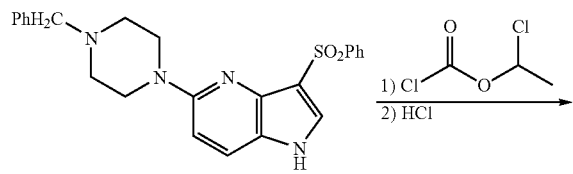

-continued

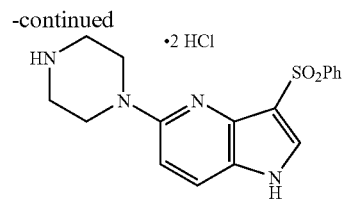

A stirred mixture of 5-(4-benzylpiperazin-1-yl)-3-(phenylsulfonyl)-1H-pyrrolo[3,2-b]pyridine (0.865 g, 2.00 mmol) and 1-chloroethylchloroformate (0.65 mL, 6.00 mmol) in 1,2-dichloroethane is heated at reflux temperature for 2.5 h under nitrogen, cooled and concentrated in vacuo, and reconcentrated from CH$_2$Cl$_2$ to a solid. This solid is heated with ethanol at reflux temperature under nitrogen for 2 h, cooled and concentrated in vacuo. The resultant residue is stirred in ethanol for 16 h and filtered. The filtercake is heated with methanol and two drops of concentrated hydrochloric acid for 30 h and concentrated in vacuo to a solid. This solid is chromatographed (silica gel, 5:95 concentrated ammonium hydroxide:ethanol as eluent) to afford the free amine of the title compound as a white solid. The free amine is dissolved in methanol, treated with 2.0 M aqueous hydrochloric acid (1.1 mL, 2.2 mmol) and concentrated to an off-white solid residue. This residue is recystallized from methanol to afford the title compound as an off-white solid, 165 mg (24% yield), mp 198-203° C. (foams), identified by NMR and mass spectral analyses.

EXAMPLE 10

Comparative Evaluation of 5-HT6 Binding Affinity of Test Compounds

The affinity of test compounds for the serotonin 5-HT6 receptor is evaluated in the following manner. Cultured Hela cells expressing human cloned 5-HT6 receptors are harvested and centrifuged at low speed (1,000×g) for 10.0 min to remove the culture media. The harvested cells are suspended in half volume of fresh physiological phosphate buffered saline solution and recentrifuged at the same speed. This operation is repeated. The collected cells are then homogenized in ten volumes of 50 mM Tris.HCl (pH 7.4) and 0.5 mM EDTA. The homogenate is centrifuged at 40,000×g for 30.0 min and the precipitate is collected. The obtained pellet is resuspended in 10 volumes of Tris.HCl buffer and recentrifuged at the same speed. The final pellet is suspended in a small volume of Tris.HCl buffer and the tissue protein content is determined in aliquots of 10-25 μl volumes. Bovine Serum Albumin is used as the standard in the protein determination according to the method described in Lowry et al., *J. Biol. Chem.*, 193:265 (1951). The volume of the suspended cell membranes is adjusted to give a tissue protein concentration of 1.0 mg/ml of suspension. The prepared membrane suspension (10 times concentrated) is aliquoted in 1.0 ml volumes and stored at −70° C. until used in subsequent binding experiments.

Binding experiments are performed in a 96 well microtiter plate format, in a total volume of 200 μl. To each well is added the following mixture: 80.0 ∞l of incubation buffer made in 50 mM Tris.HCl buffer (pH 7.4) containing 10.0 mM MgCl$_2$ and 0.5 mM EDTA and 20 μl of [$^3$H]-LSD (S.A., 86.0 Ci/mmol, available from Amersham Life Science), 3.0 nM. The dissociation constant, K$_D$ of the [$^3$H]LSD at the human serotonin 5-HT6 receptor is 2.9 nM, as determined by saturation binding with increasing concentrations of [³H]LSD. The reaction is initiated by the final addition of 100.0 μl of tissue suspension. Nonspecific binding is measured in the presence of 10.0 μM methiothepin. The test compounds are added in 20.0 μl volume.

The reaction is allowed to proceed in the dark for 120 min at room temperature, at which time, the bound ligand-receptor complex is filtered off on a 96 well unifilter with a Packard Filtermate® 196 Harvester. The bound complex caught on the filter disk is allowed to air dry and the radioactivity is measured in a Packard TopCount® equipped with six photomultiplier detectors, after the addition of 40.0 μl Microscint®-20 scintillant to each shallow well. The unifilter plate is heat-sealed and counted in a PackardTopCount® with a tritium efficiency of 31.0%.

Specific binding to the 5-HT6 receptor is defined as the total radioactivity bound less the amount bound in the presence of 10.0 μM unlabeled methiothepin. Binding in the presence of varying concentrations of test compound is expressed as a percentage of specific binding in the absence of test compound. The results are plotted as log % bound versus log concentration of test compound. Nonlinear regression analysis of data points with a computer assisted program Prism® yielded both the $IC_{50}$ and the $K_i$ values of test compounds with 95% confidence limits. A linear regression line of data points is plotted, from which the $IC_{50}$ value is determined and the $K_i$ value is determined based upon the following equation:

$$K_i = IC_{50}/(1+L/K_D)$$

where L is the concentration of the radioactive ligand used and $K_D$ is the dissociation constant of the ligand for the receptor, both expressed in nM.

Using this assay, the following Ki values are determined and compared to those values obtained by representative compounds known to demonstrate binding to the 5-HT6 receptor. The data are shown in Table I, below.

TABLE I

| Test Compound (Ex. No.) | 5-HT6 Binding Ki (nM) |
|---|---|
| 4 | 34 |
| 8 | 30 |
| 9 | 2 |
| Comparative Examples | |
| Loxapine | 41.4 |
| Mianserin | 44.2 |

What is claimed is:

1. A compound of formula I

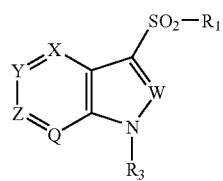

(I)

wherein
W is $CR_2$;
X is N or $CR_4$;
Y is N or $CR_5$;
Z is N or $CR_6$;
Q is N or $CR_7$ with the proviso that one and only one of X, Y, Z and Q must be N;
$R_1$ is an optionally substituted $C_1$-$C_6$alkyl, $C_3$-$C_7$cycloalkyl, aryl, or heteroaryl group or an optionally substituted 8- to 13-membered bicyclic or tricyclic ring system having a N atom at the bridgehead and optionally containing 1, 2 or 3 additional heteroatoms selected from N, O or S;
$R_2$ is H, halogen, or a $C_1$-$C_6$alkyl, $C_1$-$C_6$alkoxy, $C_3$-$C_7$cycloalkyl, aryl or heteroaryl group each optionally substituted;
$R_3$ is H or a, $C_3$-$C_7$cycloalkyl, aryl or heteroaryl group each optionally substituted;
$R_4$, $R_5$, $R_6$ and $R_7$ are each independently H, halogen, CN, $COR_8$, $OCO_2R_9$, $CO_2R_{10}$, $CONR_{11}R_{12}$, $SO_nR_{13}$, $NR_{14}R_{15}$, $OR_{16}$ or a $C_1$-$C_6$alkyl, $C_3$-$C_7$cycloalkyl, aryl or heteroaryl group each optionally substituted or a group M having the structure

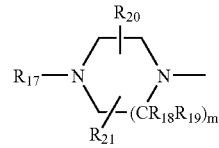

with the proviso that at least one of $R_4$, $R_5$, $R_6$ or $R_7$ must be a group M and with the further proviso that when W is $CR_2$ and X or Z is N, then $R_7$ must be other than a group M;
$R_8$, $R_9$, $R_{10}$ and $R_{13}$ are each independently H or a $C_1$-$C_6$alkyl, $C_2$-$C_6$alkenyl, $C_2$-$C_6$alkynyl, $C_3$-$C_6$cycloalkyl, cycloheteroalkyl, aryl or heteroaryl group each optionally substituted;
$R_{11}$, $R_{12}$, $R_{14}$ and $R_{15}$ are each independently H or an optionally substituted $C_1$-$C_4$alkyl group or $R_{11}$ and $R_{12}$ or $R_{14}$ and $R_{15}$ may be taken together with the atom to which they are attached to form a 5- to 7-membered ring optionally containing another heteroatom selected from O, $NR_{22}$ or $SO_n$;
$R_{16}$ is H or a $C_1$-$C_6$alkyl, $C_2$-$C_6$alkenyl, $C_2$-$C_6$alkynyl, $C_3$-$C_7$cycloalkyl, cycloheteroalkyl, aryl or heteroaryl group each optionally substituted;
n is 0 or an integer of 1 or 2;
$R_{17}$ is H or a $C_1$-$C_6$alkyl or $C_3$-$C_7$cycloalkyl group each optionally substituted;
$R_{18}$, $R_{19}$, $R_{20}$, $R_{21}$ and $R_{23}$ are each independently H or a $C_1$-$C_6$alkyl or $C_3$-$C_7$cycloalkyl group each optionally substituted;
m is 1 or 2; and
$R_{22}$ is H or a $C_1$-$C_6$alkyl, $C_2$-$C_6$alkenyl, $C_2$-$C_6$alkynyl, $C_3$-$C_7$cycloalkyl, cycloheteroalkyl, aryl or heteroaryl group each optionally substituted; or
the stereoisomers thereof or the pharmaceutically acceptable salts thereof.

2. The compound according to claim 1 wherein m is 1.

3. The compound according to claim 1 wherein Y is $CR_5$ and $R_5$ is a group M.

4. The compound according to claim 2 wherein Y is $CR_5$ and $R_5$ is a group M.

5. The compound according to claim 2 wherein $R_1$ is an optionally substituted phenyl, naphthyl or heteroaryl group.

6. The compound according to claim 5 wherein $R_5$ or $R_7$ is a group M.

7. The compound according to claim 1 selected from the group consisting of:
   5-(4-benzylpiperazin-1-yl)-3-(phenylsulfonyl)-1H-pyrrolo[2,3-b]pyridine;
   5-(4-methylpiperazin-1-yl)-3-(phenylsulfonyl)-1H-pyrrolo[2,3-c]pyridine;
   3-(phenylsulfonyl)-5-(4-propylpiperazin-1-yl)-1H-pyrrolo[2,3-b]pyridine;
   3-(phenylsulfonyl)-5-piperazin-1-yl-1H-pyrrolo[2,3-b]pyridine;
   3[-(3-cyanophenyl)sulfonyl]-5-piperazin-1-yl-1H-pyrrolo[2,3-b]pyridine;
   5-(4-benzylpiperazin-1-yl)-3-[(1-naphthyl)sulfonyl]-1H-pyrrolo[3,2-c]pyridine;
   5-(4-methylpiperazin-1-yl)-3-[(2-naphthyl)sulfonyl]-1H-pyrrolo[3,2-b]pyridine;
   3-[(2-chloro-4-fluorophenyl)sulfonyl]-5-(4-propylpiperazin-1-yl)-1H-pyrrolo[2,3-b]pyridine;
   1-methyl-3-(phenylsulfonyl)-5-piperazin-1-yl-1H-pyrrolo[3,2-b]pyridine;
   1-phenyl-3-(phenylsulfonyl)-5-piperazin-1-yl-1H-pyrrolo[2,3-c]pyridine;
   5-(4-benzylpiperazin-1-yl)-3-[(3-fluorophenyl)sulfonyl]-1H-pyrrolo[3,2-c]pyridine;
   3-[(4-fluorophenyl)sulfonyl]-5-(4-methylpiperazin-1-yl)-1H-pyrrolo[3,2-b]pyridine;
   3-[(2-chlorophenyl)sulfonyl]-5-(4-propylpiperazin-1-yl)-1H-pyrrolo[2,3-b]pyridine;
   3-[(4-aminophenyl)sulfonyl]-5-piperazin-1-yl-1H-pyrrolo[2,3-b]pyridine;
   2-methyl-3-(phenylsulfonyl)-5-piperazin-1-yl-1H-pyrrolo[2,3-b]pyridine;
   4-chloro-3-(phenylsulfonyl)-5-piperazin-1-yl-1H-pyrrolo[2,3-b]pyridine;
   7-fluoro-3-(phenylsulfonyl)-5-piperazin-1-yl-1H-pyrrolo[2,3-b]pyridine;
   6-fluoro-3-(phenylsulfonyl)-5-piperazin-1-yl-1H-pyrrolo[2,3-c]pyridine;
   6-(4-benzylpiperazin-1-yl)-3-(phenylsulfonyl)-1H-pyrrolo[3,2-c]pyridine;
   6-(4-methylpiperazin-1-yl)-3-(phenylsulfonyl)-1H-pyrrolo[3,2-b]pyridine;
   3-(phenylsulfonyl)-6-(4-propylpiperazin-1-yl)-1H-pyrrolo[2,3-b]pyridine;
   3-(phenylsulfonyl)-6-piperazin-1-yl-1H-pyrrolo[2,3-b]pyridine;
   4-(4-benzylpiperazin-1-yl)-3-(phenylsulfonyl)-1H-pyrrolo[2,3-b]pyridine;
   4-(4-methylpiperazin-1-yl)-3-(phenylsulfonyl)-1H-pyrrolo[2,3-b]pyridine; and
   3-(phenylsulfonyl)-4-(4-propylpiperazin-1-yl)-1H-pyrrolo[3,2-c]pyridine; or
   3-(phenylsulfonyl)-4-piperazin-1-yl-1H-pyrrolo[3,2-b]pyridine;
   a stereoisomer thereof; or
   a pharmaceutically acceptable salt thereof.

8. A pharmaceutical composition which comprises a pharmaceutically acceptable carrier and an effective amount of a compound of formula I

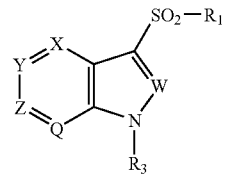

wherein
W is $CR_2$;
X is N or $CR_4$;
Y is N or $CR_5$;
Z is N or $CR_6$;
Q is N or $CR_7$ with the proviso that one and only one of X, Y, Z and Q must be N;
$R_1$ is an optionally substituted $C_1$-$C_6$alkyl, $C_3$-$C_7$cycloalkyl, aryl, or heteroaryl group or an optionally substituted 8- to 13-membered bicyclic or tricyclic ring system having a N atom at the bridgehead and optionally containing 1, 2 or 3 additional heteroatoms selected from N, O or S;
$R_2$ is H, halogen, or a $C_1$-$C_6$alkyl, $C_1$-$C_6$alkoxy, $C_3$-$C_7$cycloalkyl, aryl or heteroaryl group each optionally substituted;
$R_3$ is H or a, $C_3$-$C_7$cycloalkyl, aryl or heteroaryl group each optionally substituted;
$R_4$, $R_5$, $R_6$ and $R_7$ are each independently H, halogen, CN, $COR_8$, $OCO_2R_9$, $CO_2R_{10}$, $CONR_{11}R_{12}$, $SO_nR_{13}$, $NR_{14}R_{15}$, $OR_{16}$ or a $C_1$-$C_6$alkyl, $C_3$-$C_7$cycloalkyl, aryl or heteroaryl group each optionally substituted or a group M having the structure

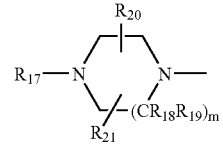

with the proviso that at least one of $R_4$, $R_5$, $R_6$ or $R_7$ must be a group M and with the further proviso that when W is $CR_2$ and X or Z is N, then $R_7$ must be other than a group M;
$R_8$, $R_9$, $R_{10}$ and $R_{13}$ are each independently H or a $C_1$-$C_6$alkyl, $C_2$-$C_6$alkenyl, $C_2$-$C_6$alkynyl, $C_3$-$C_6$cycloalkyl, cycloheteroalkyl, aryl or heteroaryl group each optionally substituted;
$R_{11}$, $R_{12}$, $R_{14}$ and $R_{15}$ are each independently H or an optionally substituted $C_1$-$C_4$alkyl group or $R_{11}$ and $R_{12}$ or $R_{14}$ and $R_{15}$ may be taken together with the atom to which they are attached to form a 5- to 7-membered ring optionally containing another heteroatom selected from O, $NR_{22}$ or $SO_n$;
$R_{16}$ is H or a $C_1$-$C_6$alkyl, $C_2$-$C_6$alkenyl, $C_2$-$C_6$alkynyl, $C_3$-$C_7$cycloalkyl, cycloheteroalkyl, aryl or heteroaryl group each optionally substituted;
n is 0 or an integer of 1 or 2;
$R_{17}$ is H or a $C_1$-$C_6$alkyl or $C_3$-$C_7$cycloalkyl group each optionally substituted;
$R_{18}$, $R_{19}$, $R_{20}$, $R_{21}$ and $R_{23}$ are each independently H or a $C_1$-$C_6$alkyl or $C_3$-$C_7$cycloalkyl group each optionally substituted;
m is 1 or 2; and $R_{22}$ is H or a $C_1$-$C_6$alkyl, $C_2$-$C_6$alkenyl, $C_2$-$C_6$alkynyl, $C_3$-$C_7$cycloalkyl, cycloheteroalkyl, aryl or heteroaryl group each optionally substituted; or the stereoisomers thereof or the pharmaceutically acceptable salts thereof.

9. The composition according to claim 8 having a formula I compound wherein m is 1.

10. The composition according to claim 9 having a formula I compound wherein Y is $CR_5$ and $R_5$ is a group M.

11. The composition according to claim 9 having a formula I compound wherein $R_1$ is an optionally substituted phenyl, naphthyl or heteroaryl group.

12. The composition according to claim 8 having a formula I compound selected from the group consisting of:

5-(4-benzylpiperazin-1-yl)-3-(phenylsulfonyl)-1H-pyrrolo[2,3-b]pyridine;

5-(4-methylpiperazin-1-yl)-3-(phenylsulfonyl)-1H-pyrrolo[2,3-c]pyridine;

3-(phenylsulfonyl)-5-(4-propylpiperazin-1-yl)-1H-pyrrolo[2,3-b]pyridine;

3-(phenylsulfonyl)-5-piperazin-1-yl-1H-pyrrolo[2,3-b]pyridine;

3[-(3-cyanophenyl)sulfonyl]-5-piperazin-1-yl-1H-pyrrolo[2,3-b]pyridine;

5-(4-benzylpiperazin-1-yl)-3-[(1-naphthyl)sulfonyl]-1H-pyrrolo[3,2-c]pyridine;

5-(4-methylpiperazin-1-yl)-3-[(2-naphthyl)sulfonyl]-1H-pyrrolo[3,2-b]pyridine;

3-[(2-chloro-4-fluorophenyl)sulfonyl]-5-(4-propylpiperazin-1-yl)-1H-pyrrolo[2,3-b]pyridine;

1-methyl-3-(phenylsulfonyl)-5-piperazin-1-yl-1H-pyrrolo[3,2-b]pyridine;

1-phenyl-3-(phenylsulfonyl)-5-piperazin-1-yl-1H-pyrrolo[2,3-c]pyridine;

5-(4-benzylpiperazin-1-yl)-3-[(3-fluorophenyl)sulfonyl]-1H-pyrrolo[3,2-c]pyridine;

3-[(4-fluorophenyl)sulfonyl]-5-(4-methylpiperazin-1-yl)-1H-pyrrolo[3,2-b]pyridine;

3-[(2-chlorophenyl)sulfonyl]-5-(4-propylpiperazin-1-yl)-1H-pyrrolo[2,3-b]pyridine;

3-[(4-aminophenyl)sulfonyl]-5-piperazin-1-yl-1H-pyrrolo[2,3-b]pyridine;

2-methyl-3-(phenylsulfonyl)-5-piperazin-1-yl-1H-pyrrolo[2,3-b]pyridine;

4-chloro-3-(phenylsulfonyl)-5-piperazin-1-yl-1H-pyrrolo[2,3-b]pyridine;

7-fluoro-3-(phenylsulfonyl)-5-piperazin-1-yl-1H-pyrrolo[2,3-b]pyridine;

6-fluoro-3-(phenylsulfonyl)-5-piperazin-1-yl-1H-pyrrolo[2,3-c]pyridine;

6-(4-benzylpiperazin-1-yl)-3-(phenylsulfonyl)-1H-pyrrolo[3,2-c]pyridine;

6-(4-methylpiperazin-1-yl)-3-(phenylsulfonyl)-1H-pyrrolo[3,2-b]pyridine;

3-(phenylsulfonyl)-6-(4-propylpiperazin-1-yl)-1H-pyrrolo[2,3-b]pyridine;

3-(phenylsulfonyl)-6-piperazin-1-yl-1H-pyrrolo[2,3-b]pyridine;

4-(4-benzylpiperazin-1-yl)-3-(phenylsulfonyl)-1H-pyrrolo[2,3-b]pyridine;

4-(4-methylpiperazin-1-yl)-3-(phenylsulfonyl)-1H-pyrrolo[2,3-b]pyridine; and 3-(phenylsulfonyl)-4-(4-propylpiperazin-1-yl)-1H-pyrrolo[3,2-c]pyridine; or 3-(phenylsulfonyl)-4-piperazin-1-yl-1H-pyrrolo[3,2-b]pyridine;

a stereoisomer thereof; or a pharmaceutically acceptable salt thereof.

\* \* \* \* \*